United States Patent
Querleux et al.

(10) Patent No.: US 7,061,617 B2
(45) Date of Patent: Jun. 13, 2006

(54) METHOD OF DETERMINING THE CAPACITY OF A COSMETIC TO DIFFUSE AND/OR ABSORB LIGHT

(75) Inventors: Bernard Querleux, Le Perreux (FR); Hervé Saint-Jalmes, Lyons (FR)

(73) Assignee: L'Oreal (FR)

( * ) Notice: Subject to any disclaimer, the term of this patent is extended or adjusted under 35 U.S.C. 154(b) by 273 days.

(21) Appl. No.: 10/458,172

(22) Filed: Jun. 10, 2003

(65) Prior Publication Data

US 2004/0042013 A1 Mar. 4, 2004

(30) Foreign Application Priority Data

Jun. 10, 2002 (FR) .................................. 02 07108

(51) Int. Cl.
*G01N 21/55* (2006.01)
(52) U.S. Cl. ..................................... 356/446
(58) Field of Classification Search ........ 356/445–448, 356/402, 408, 416, 425
See application file for complete search history.

(56) References Cited

U.S. PATENT DOCUMENTS

| 5,781,289 A | 7/1998 | Sabsabi et al. |
| 5,923,039 A | 7/1999 | Jablonski et al. |
| 6,015,969 A * | 1/2000 | Nathel et al. ............ 250/227.27 |
| 6,205,354 B1 * | 3/2001 | Gellermann et al. ........ 600/477 |
| 2002/0087085 A1 * | 7/2002 | Dauga ........................ 600/476 |

FOREIGN PATENT DOCUMENTS

| DE | 297 19 497 U | 8/1998 |
| EP | 0 993 601 | 4/2000 |
| EP | 1 156 074 A1 | 11/2001 |
| WO | WO-95 05892 A1 | 3/1995 |
| WO | WO-02 057726 A2 | 7/2002 |

OTHER PUBLICATIONS

Gobin, "Integrating the digitized backscattered image to measure absorption and reduced-scattering coefficients in vivo", Applied Optics, vol. 38, No. 19, pp. 4217-4227, Jul. 1, 1999.
Patent Abstracts of Japan, vol. 1995, No. 10, Nov. 30, 1995 & JP 07 167781 9 SHISEIDO CO LTD), Jul. 4, 1995.

* cited by examiner

*Primary Examiner*—Michael P. Stafira
(74) *Attorney, Agent, or Firm*—Lerner, David, Littenberg, Krumholz & Mentlik, LLP

(57) ABSTRACT

Methods and apparatus for determining the optical characteristics of cosmetic substances are disclosed. The method includes illuminating the surface of the substance with an incident light beam so as to form a back-scatter spot, obtaining an image of the back-scatter spot, and analyzing the variations in brightness of the image at a number of points so as to determine the optical characteristic in question.

57 Claims, 2 Drawing Sheets

METHOD OF DETERMINING THE CAPACITY OF A COSMETIC TO DIFFUSE AND/OR ABSORB LIGHT

FIELD OF THE INVENTION

The present invention relates to a method of determining the magnitude of a characteristic of the optical behavior of a surface on which a cosmetic has been applied, in particular of the skin and/or of keratinous fibers. More particularly, the present invention also relates to apparatus for implementing the above method.

BACKGROUND OF THE INVENTION

The term "cosmetic" is used to cover any substance as defined in EEC Directive 76/768 as amended by Directive 93/35 of Jun. 14, 1993.

The article "Integrating the digitized back-scattered image to measure absorption of reduced-scattering coefficients in vivo" by Gobin et al., published in the journal Applied Optics, of Jul. 1, 1999, describes measurements of diffusion and absorption coefficients performed in the laboratory on bare skin.

SUMMARY OF THE INVENTION

In accordance with the present invention, methods for determining an optical characteristic of a substance have been discovered comprising illuminating the surface of the substance with an incident light beam so as to form a back-scatter spot including a center, obtaining an image of the back-scatter spot, and analyzing the variations in brightness of the image at a plurality of points so as to determine the optical characteristic. Preferably, the optical characteristic comprises the capacity of the substance to diffuse or absorb light. In a preferred embodiment, the substance comprises a cosmetic substance, such as a dermatological substance. In a preferred embodiment, the method includes applying the cosmetic substance to a support.

In accordance with one embodiment of the method of the present invention, the method includes determining a reduced diffusion coefficient as a function of the variation in brightness of the plurality of points. Preferably, at least two of the plurality of points are located at different distances from the center.

In accordance with another embodiment of the method of the present invention, the method includes determining the absorption coefficient as a function of the variation in brightness at the plurality of points. Preferably, at least two of the plurality of points are located at different distances from the center.

In accordance with one embodiment of the method of the present invention, the support comprises keratinous fibers or cells. In another embodiment, the support comprises an inert support. In yet another embodiment, the support comprises a relief, and preferably the support is substantially planar.

In accordance with one embodiment of the method of the present invention, the cosmetic substance is disposed on the support over an area of between about 0.5 and 5.0 cm$^2$, and preferably between about 1 and 2 cm$^2$.

In accordance with another embodiment of the method of the present invention, the incident light beam has a substantially constant intensity over its entire cross-section. Preferably, the incident light beam is produced by a light source, and the method includes placing a spatial filter between the light source and the cosmetic substance.

In accordance with another embodiment of the method of the present invention, the cosmetic substance comprises a substance suitable for modifying at least one physico-chemical property of the support.

In accordance with the present invention, a method has also been devised for determining at least one characteristic of a cosmetic substance comprising illuminating a first surface and a second surface with an incident light beam so as to form back-scatter spots, obtaining images of the back-scatter spots representing the first and second surfaces, analyzing the variation in brightness of the images at a plurality of points corresponding to the first and second surfaces, and determining the at least one characteristic as a function of the variations in brightness corresponding to the first and second surfaces, the first surface comprising skin or keratinous fibers and the second surface comprising the cosmetic substance applied to the skin or keratinous fibers. Preferably, the at least one characteristic comprises an optical characteristic comprising the capacity of the cosmetic surface to diffuse or absorb light.

In accordance with another embodiment of the present invention, a method has been discovered for determining variations in at least one optical characteristic of a cosmetic substance over time comprising applying the cosmetic substance to a support to provide a surface of the cosmetic substance, illuminating the surface of the cosmetic substance with an incident light beam so as to form a back-scatter spot, obtaining a first image of the back-scatter spot at a first instant, analyzing the variation in the brightness of the first image at a plurality of points so as to determine the at least one optical characteristic at a first instant, obtaining a second image of the back-scatter spot at a second instant, analyzing the variation in the brightness of the second image at a plurality of points so as to determine the at least one optical characteristic at a second instant, and determining the at least one optical characteristic over time as a function of the analyses of the variation in the brightness of the first and second images. Preferably, the effecting of the surface comprises washing the surface, exposing the surface to wind, and contacting the surface with UV radiation.

In accordance with the present invention, a method has also been discovered for prescribing a cosmetic substance to be applied to the skin comprising illuminating the skin with an incident light beam so as to form a back-scatter spot, obtaining an image of the back-scatter spot, analyzing the variation in brightness at a plurality of points so as to determine at least one characteristic representing the capacity of the skin to diffuse or absorb light, and prescribing the cosmetic substance having a capacity to diffuse or absorb light corresponding to the predetermined at least one characteristic.

In accordance with the present invention, apparatus has also been discovered for determining the capacity of a cosmetic substance to diffuse or absorb light comprising a light source for delivering a light beam capable of forming a light spot having a center on a predetermined surface, a camera for obtaining at least one image of the light spot, and an analyzer for analyzing the variation in brightness of the at least one image at a plurality of points of the light source so as to determine at least one data point representing the capacity of the cosmetic substance to diffuse or absorb light. In a preferred embodiment, at least two of the plurality of points are located different distances from the center.

In accordance with the present invention, a method has also been discovered for preparing a cosmetic substance for application to the skin comprising illuminating a predetermined area of the skin with an incident light beam so as to form a back-scatter spot, obtaining an image of the back-scatter spot, analyzing the variation in brightness of the image at a plurality of points so as to determine at least one data point representing the capacity of the skin to diffuse or absorb light, and preparing the cosmetic substance based upon the at least one data point. Preferably, the cosmetic substance has the capacity to diffuse or absorb light corresponding to the capacity of the skin to diffuse or absorb light.

In accordance with one aspect of the present invention, a method is provided for determining the capacity for diffusing and/or absorbing light of a cosmetic or dermatological product optionally applied on a support, the method comprising the following steps:

a) illuminating the substance and/or a zone of the support on which the substance has been applied with an incident light beam in such a manner as to form a back-scatter spot;

b) acquiring an image of the spot; and c) analyzing the image as a function of variation in brightness between the various points of the spot to determine at least one item of information representative of the capacity for diffusing light and/or absorbing it of the substance and/or the support in the presence of the substance.

By way of example, the substance illuminated by the incident light beam may form a relatively thick mass, e.g. being contained in a receptacle. It can also form a layer on the surface of a support, where such a layer can be relatively thin. The substance may also be absorbed by a support.

As one implementation of the present invention, it is thus possible as a function of variation in the brightness of various points of the spot, and in particular of points situated at different distances from the center of the spot, to determine a reduced diffusion coefficient ($\mu'_s$). In a variant, or additionally, it is also possible to determine an absorption coefficient ($\mu_a$).

The support may comprise keratinous cells and/or fibers. The support may be inert or living.

The surface illuminated by the incident light beam may be substantially plane or it may present relief.

The substance may have been applied on the support to cover an area, for example an area lying in the range of between about 0.5 square centimeters ($cm^2$) and 5 $cm^2$, and in particular in the range of between about 1 $cm^2$ and 2 $cm^2$.

The incident light beam may be a beam of white light, or in a variant, it may be a beam of monochromatic light, in particular visible light, e.g. of red or blue color. Its wavelength may be selected as a function of the nature of the support and/or of the optical properties that are to be determined, for example. The light beam may be a beam of coherent light.

The section of the light beam may be less than or equal to 4 micrometers ($\mu m$), and preferably less about than 2 $\mu m$.

The intensity of the incident light beam is preferably substantially constant over its entire section. Since the incident light beam is produced by a light source, a spatial filter may be placed between the source and the substance.

The angle of incidence of the incident light beam relative to the normal of the surface of the substance may lie in the range of from about 5° to 25°, for example, and in particular in the range of from about 10° to 20°.

Where appropriate, a mirror may be placed on the path of the incident light beam.

Advantageously, a device without a mirror can be used for in vivo measurements.

The image may be acquired in various ways, for example by means of a camera, in particular a monochrome charge-coupled device (CCD) camera.

Data processing may be performed locally, but in a variant it is possible to transmit the acquired image remotely, in particular over the Internet, to a processing center for analysis purposes.

The image may be acquired through an optical system having variable magnification. This makes it possible to enlarge the image so that it occupies a majority of the sensing area so as to benefit from best resolution.

A polarizer may be placed on the path of the incident light beam, between the source and the substance, and the image may be acquired through an analyzer placed between the substance and the camera.

The spot may be observed in the absence of any interfering light, however the incident light beam may be modulated and the image may be acquired synchronously, thus making it possible to take measurements in the presence of interfering light.

The substance may be applied to the support so as to have thickness, in particular substantially constant thickness, lying in the range of from about 7 $\mu m$ to 20 $\mu m$, for example.

The substance may be of uniform composition.

By way of example, the substance may be selected from the following: foundation makeup, sunscreen, depigmenting cream, antiwrinkle cream, moisturizer, this list not being limiting.

The substance may be suitable for modifying at least one physico-chemical property of the support on which it is applied, as is the case for example of a depigmenting cream.

In another of its aspects, the present invention also provides a method of determining a characteristic of a cosmetic substance, the method comprising the steps of:

determining the capacities of two surfaces to diffuse and/or absorb light, the surfaces constituting respectively:
 a) a substance applied to the skin and/or the keratinous fibers; and
 b) the skin and/or keratinous fibers in the absence of the substance, by performing for each such surface at least the following steps:

i) illuminating a zone of the surface in question with an incident light beam in such a manner as to form a back-scatter spot;

ii) acquiring an image of the spot; and iii) analyzing the image as a function of variation in brightness at various points of the spot in order to determine at least one item of information representative of the capacity of the substance, the skin, and/or the keratinous fibers to diffuse light and/or to absorb it; and:

determining at least one characteristic of the substance as a function of the information obtained for the skin and/or the keratinous fibers with and without the substance.

The characteristic of the substance as determined in this way may be its covering ability or its staying power. When the substance is a sunscreen, the characteristic which is determined may be the effectiveness of the protection conferred thereby.

With a depigmenting cream, the characteristic which is determined may be the effectiveness thereof.

In another of its aspects, the present invention also provides a method of determining how a characteristic of a cosmetic substance varies over time, the method comprising the following steps:

a) applying the substance on a support;

b) illuminating a zone of the support on which the substance has been applied with an incident light beam in such a manner as to form a back-scatter spot;

c) acquiring a first image of the spot;

d) analyzing the first image as a function of variation in brightness at various points of the spot to determine at least one item of information representative of the capacity of the substance to diffuse light and/or to absorb it at a first instant;

e) acquiring a second image of the spot at a second instant;

f) analyzing the second image as a function of variation in the brightness at various points of the spot to determine at least one item of information representative of the capacity of the substance to diffuse light and/or to absorb it, at the second instant; and g) determining how a characteristic of the substance varies over time as a function of the information obtained during steps d) and f).

In one implementation of the present invention, the method may include the following step between steps d) and e):

exerting some action on the substance and/or the support.

By way of example, this action may be washing the support. This may make it possible, for example, to determine the ability of sunscreen or makeup to withstand water. Some other action may be exerted, for example exposure to the wind or to ultraviolet radiation or contact with an element onto which the makeup is to be transferred.

In another of its aspects, the present invention provides a method of prescribing or preparing a cosmetic substance, the method comprising the following steps:

a) illuminating a zone of the skin with an incident light beam so as to form a back-scatter spot;

b) acquiring an image of the spot;

c) analyzing the image as a function of variation in brightness at various points of the spot to determine at least one item of information representative of the capacity of the skin to diffuse light and/or to absorb it;

d) prescribing, at least as a function of the item of information, a cosmetic substance, in particular a substance having the capacity to diffuse light and/or to absorb light close to the capacity previously determined for the skin.

The cosmetic substance as prepared or prescribed in this way may be intended, for example, for masking imperfections of the skin and for achieving natural makeup.

The present invention also provides apparatus for determining the capacity of a cosmetic substance for diffusing and/or absorbing light, which apparatus may comprise:

a source suitable for delivering a light beam capable of forming a light spot on the substance or on a support on which a substance has been applied;

a camera, in particular a monochrome CCD camera, enabling at least one image of the spot to be acquired; and an analyzer apparatus for analyzing the image as a function of variation in brightness at various points of the spot, in particular at points situated at different distances from the center of the spot, to determine at least one item of information representative of the capacity of the substance to diffuse light and/or to absorb it.

The light source may comprise a laser.

The apparatus may include a spatial filter through which the light beam passes, and where appropriate a mirror placed on the path of the light beam.

The light source may be capable of emitting at at least two different wavelengths, optionally simultaneously.

The analysis apparatus may be configured to receive the image acquired by the camera by means of a network, in particular the Internet.

BRIEF DESCRIPTION OF THE DRAWINGS

The present invention can be better understood on reading the following detailed description which, in turn, refers to the accompanying drawings, in which.

DETAILED DESCRIPTION

In one of its aspects, the present invention serves to determine at least one reduced diffusion coefficient ($\mu'_s$) and/or at least one light absorption coefficient ($\mu_a$) by observing a surface on which a cosmetic substance has been applied.

The reduced diffusion coefficient $\mu'_s$ represents the change in the spatial distribution of a beam deflected in multiple directions by a surface or by a medium, without change to the frequencies of the monochromatic rays making it up.

The absorption coefficient $\mu_a$ represents the decrease in the intensity of the beam on going through a material, its radiant energy having been transformed into some other form of energy.

Figure 1:
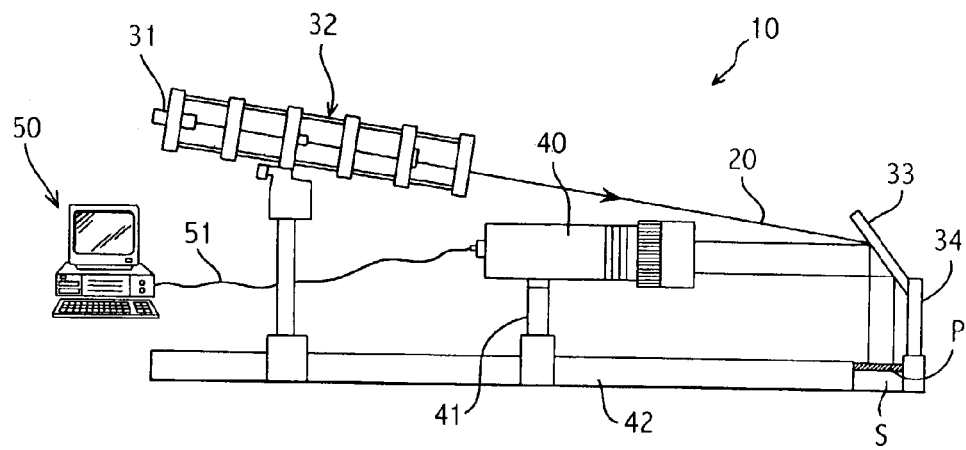
FIG. 1 is a side, elevational, simplified diagrammatic view of apparatus enabling an example of the method of the present invention to be implemented.

FIG. 1 shows apparatus 10 for determining a value that is representative of the capacity of a cosmetic substance P for diffusing light and/or for absorbing light. The cosmetic substance P is applied to a support S, which may be constituted for example by an inert support, by human skin, or keratinous fibers, this list of such supports, however, not being limiting.

In the example shown, the substance P is applied on the support S at a thickness lying in the range of from about 10 μm to 15 μm.

A zone of the support S covered with the substance P is illuminated with an incident light beam 20 in order to form a back-scatter spot.

In the example described, the light beam 20 is monochromatic, being delivered by a laser 31.

In the example described, the wavelength produced by the laser is about 635 nanometers (nm), however it would not go beyond the ambit of the present invention for the incident light beam to be produced by some other type of source and to present a different wavelength, for example in the blue or the UV regions of the spectrum. By way of example, it is also possible to use as the light source a helium neon (HeNe) laser, one or more light-emitting diodes (LEDs), or a source of white light.

The light beam 20 passes through a spatial filter 32 serving to obtain uniform distribution of the light intensity of the beam.

In the example described, the support S onto which the substance P has been applied is placed horizontally and the laser 31 slopes at a small angle relative to the horizontal. To illuminate the support S with a light beam that slopes at a small angle relative to the normal, a mirror 35 is placed in the path of the incident beam 20, the mirror being inclined at about 45° relative to the vertical. The orientation of the incident light beam may possibly be modified by varying the inclination of the mirror 33 relative to the structure 34.

Figure 2:
FIG. 2 is a top, elevational view of an example of the image of a back-scatter spot on the skin after a cosmetic substance has been applied.

A camera 40 is used to acquire a digital image of the spot formed by the light beam after being reflected in the mirror 33, and an example of such an image is shown in FIG. 2. In this example, the cosmetic is a foundation makeup.

Figure 3:
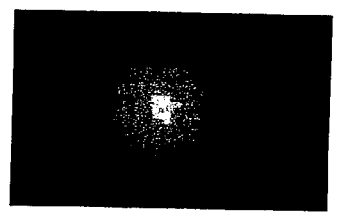
FIG. 3 is a top, elevational view of an example of the image of a back-scatter spot on the skin before a cosmetic substance has been applied.

FIG. 3 shows an example of a digital image of the spot formed on the skin prior to applying the cosmetic.

In the example described, the camera is a monochromatic CCD camera having a resolution of 490 by 660 pixels, but it would not go beyond the ambit of the present invention to use a camera having a different resolution, and possibly a color camera.

The camera is fixed on a stand 41 that is movable along a guide 42 parallel to the support S, thus making it possible to adjust the distance between its lens and the support S.

When the substance P applied on the support S is illuminated with a light beam of short wavelength, the back-scatter spot is relatively small since there is more absorption.

Under such circumstances, the image can be enlarged by reducing the distance between the lens and the sample.

In a variant, the camera may be provided with a lens providing variable magnification, enabling the size of the back-scatter spot to be matched to the size of the light-sensitive area.

The information picked up by the camera is transmitted to a computer 50 by a cable 51.

The computer 50 is configured to calculate values that are representative of the capacity of the substance to diffuse and/or absorb light on the basis of the brightness of each pixel in the digital image. The computer 50 can thus be programmed to calculate absorption and diffusion coefficients.

Reflectance R(r,φ), i.e. the ratio of the intensity of the reflected light over the intensity of the incident light, can be calculated as a function of cylindrical coordinates starting from the center of the spot.

Integrating R(r,φ) as a function of φ, the function $\overline{R}(r)$ is obtained:

$$\overline{R}(r) = \oint R(r, \varphi) \frac{d\varphi}{2\pi}$$

Figure 4:
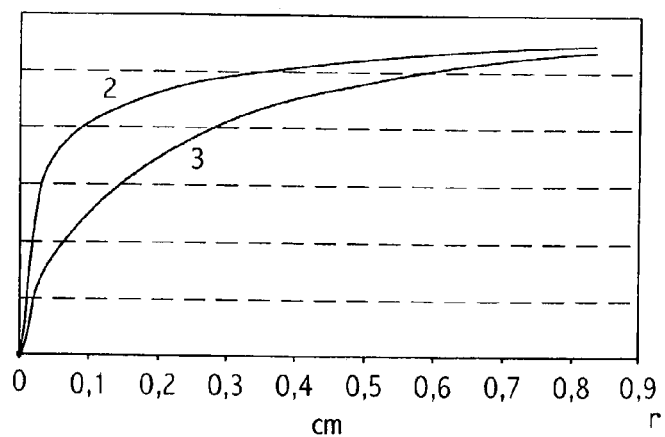
FIG. 4 is a graphical representation for calculating reduced diffusion and absorption coefficients.

FIG. 4 shows the value of the reflectance $\overline{R}$ of the spot integrated as a function of radius r:

$$Rint(r) = \int_0^r R(\rho) 2\pi\rho \cdot d\rho$$

A function of the radius is obtained having constants which give access to diffusion and absorption coefficients:

$$Rint(r) = a\left[1 - \exp\left(-\frac{r}{b}\right)\right]$$

with $$a = a_1 \exp\left[-a_2\left(1 + \frac{\mu'_s}{\mu_a}\right)^{-0.5}\right]$$

$$b = \left[b_1 + b_2 \ln\left(\frac{\mu_a}{\mu'_s}\right)\right]\mu'_s{}^{-1}$$

and where $a_1$, $a_2$, $b_1$, and $b_2$ depend only on refractive index n. For curve 2 corresponding to the spot of FIG. 2 obtained after applying foundation makeup, the following values are obtained: $\mu_a$=2.82 cm$^{-1}$ and $\mu'_s$=94.72 cm$^{-1}$, and for curve 3 corresponding to the spot of FIG. 3 obtained prior to applying the substance, the following values are obtained: $\mu_a$=1.11 cm$^{-1}$ and $\mu'_s$=28.77 cm$^{-1}$.

The image of the spot may be subtracted from a black image in order to cancel out statistically a large fraction of thermal noise.

It would not go beyond the ambit of the present invention for at least one polarizer to be placed in the path of the incident light beam between the source and the cosmetic, and/or in the path of the back-scattered light between the cosmetic and the camera.

Figure 5:
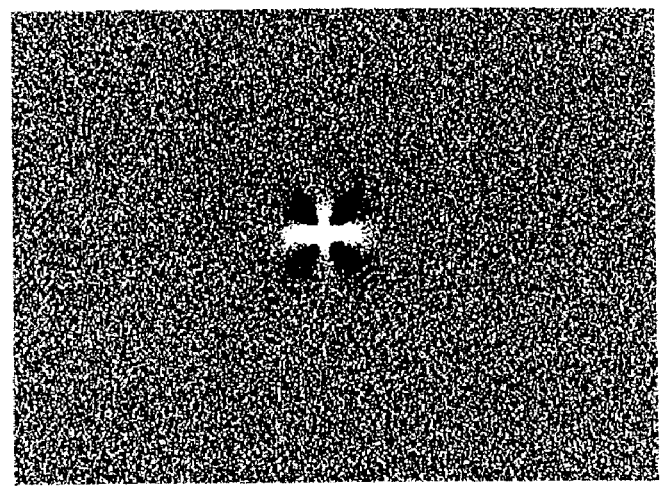
FIG. 5 is a top, elevational view of an example of an image that results from taking the difference between images obtained in incident light that is horizontally polarized and back-scattered light that is polarized horizontally or vertically.

By way of example, FIG. 5 is a normalized image that results from taking the difference between images obtained by polarizing the incident light beam horizontally and by polarizing the back-scattered light beam firstly horizontally and/or secondly vertically.

This operation makes it possible to calculate two additional optical parameters, namely the anisotropy coefficient g and the pure diffusion coefficient $\mu_s$.

For this purpose, three images are acquired: the first without polarization, the second with the incident light and the back-scattered light both polarized horizontally, and the third by polarizing the incident light horizontally and the back-scattered light vertically.

The first image makes it possible to calculate the absorption coefficient $\mu_a$ and the reduced diffusion coefficient $\mu'_s$, as explained above, and the other two images makes it possible to calculate the anisotropy coefficient g and $\mu_s$ by calculating $\mu'_s$.

It would not go beyond the ambit of the present invention to use portable apparatus for acquiring the image of the back-scatter spot.

Figure 6:
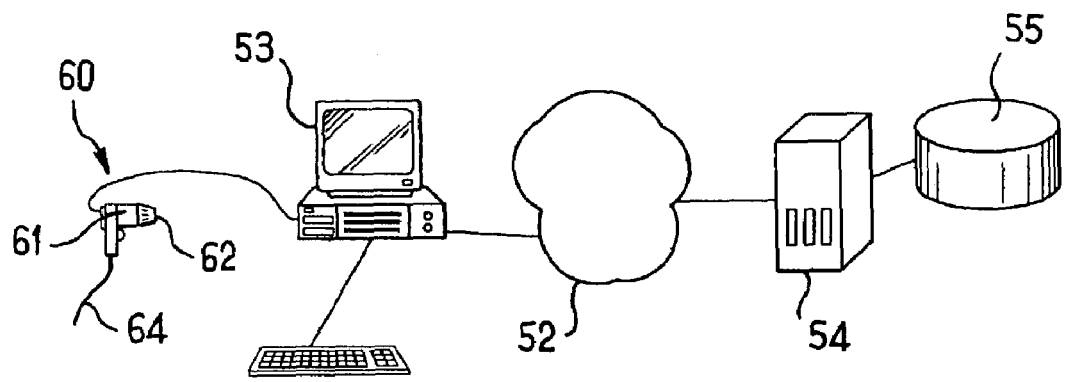
FIG. 6 is a side, elevational, simplified diagrammatic view of other apparatus enabling an example of the method of the present invention to be implemented.

By way of example, FIG. 6 shows portable apparatus 60 comprising a light source and a camera, e.g. of the webcam type, placed in a unit 61. The unit 61 has an opening 62 through which the light beam 20 coming from the light source exits, and through which the image is acquired by the camera.

The data picked up by the camera can be transmitted by means of a computer 53 over a network 52, in particular the Internet, to a processing center 54 connected to a database 55 and configured to process the transmitted information and to calculate the reduced diffusion coefficient and the absorption coefficient.

The processing center 54 may also be programmed to respond to the transmitted data and the calculations performed to make a diagnosis and to recommend a suitable cosmetic or care product and to give advice.

The processing center 54 may also be arranged to enable a variety of data to be gathered, for example in order to make up a data bank containing characteristics representative of the capacities of different cosmetic substances for diffusing and/or absorbing light.

The portable apparatus 60 may be present in a beauty parlor or at a point of sale, for example, and may be used for the purpose of providing personalized cosmetics and/or care products, in particular as a function of a client's skin type and/or keratinous fibers.

The substance whose optical characteristics are determined may be a foundation makeup, for example.

Under such circumstances, the reduced diffusion coefficient and the absorption coefficient of bare skin can be initially calculated. Thereafter foundation makeup is applied to the skin and the reduced diffusion coefficient and the absorption coefficient are measured on the skin to which the foundation layer has been applied. By comparing the values obtained before and after applying the foundation to the skin, it is possible to evaluate the covering ability of the foundation.

It is also possible to characterize the match between the foundation and the skin by proceeding in a similar manner. The reduced diffusion coefficient and the absorption coefficient of the skin before and after applying the foundation are calculated, and by comparing these values, information is obtained concerning the capacity of the foundation for achieving natural makeup.

The invention also makes it possible to recommend a substance that matches a particular type of skin or of keratinous fibers.

To do this, the data bank 55 may contain characteristic values for light diffusion and/or absorption of a range of substances. Thereafter, for a particular individual, it is possible, e.g. by using the apparatus 60, to determine values that are characteristics of the light absorption and/or diffusion of that person's skin and/or keratinous fibers. These values can be compared with values stored in the data bank 55, and the processing center 54 can be configured to determine which substance is most suitable for the individual and to send this result to the computer 53 over the network 52.

In another implementation, it is possible to initially apply the substance to a support, and then take a first image at a first instant and calculate the reduced diffusion coefficient and/or the absorption coefficient for a first time. Thereafter, a second image is taken at a second instant, for example spaced apart from the first by a time interval of about one hour, and the reduced diffusion coefficient and the absorption coefficient of the substance are calculated a second time. By comparing these values during an evaluation step it is possible to determine how the characteristic light absorption and diffusion values vary over time.

This makes it possible to measure the persistence of a cosmetic, for example.

Between the first measurement and the second measurement, it is also possible to take some action, for example seeking to remove the substance. It may be constituted, for example, by a sunscreen which is applied to the skin and the action can be washing. It is thus possible to determine the ability of the sunscreen to withstand water, for example.

The action taken may also be an action that serves to modify the physical and/or chemical properties of the substance and/or of the support, in particular the skin. Thus, for example, it is possible to characterize the effectiveness of the protection provided by a sunscreen during exposure to UV radiation, for example, by taking account of the reactions of the epidermis that can interact with the substance.

The substance may also be a depigmenting cream. It is then possible to measure the variation in skin pigment over time after the depigmenting cream has been applied to the skin in order to characterize its effectiveness.

The substance may also be an antiwrinkle cream or a moisturizer.

The present invention also makes it possible to determine characteristic values for the diffusion and the absorption of a substance applied to an inert support, to the skin, or to keratinous fibers, during the development of the formulation of the substance in order to determine the influence of adding certain ingredients so that the formulation can be modified accordingly, where appropriate.

Naturally, the present invention is not limited to the examples described above.

Thus, it would not go beyond the ambit of the present invention to calculate values representative of the capacity of a substance to diffuse and/or absorb light other than the reduced diffusion coefficient $\mu'_s$ and the absorption coefficient $\mu_a$.

It is also possible to combine the characteristics of the various above-described implementations with one another.

Throughout the description, the term "comprises a" should be understood as being synonymous with "comprises at least one", unless specified to the contrary.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for determining an optical characteristic of a substance comprising illuminating the surface of said substance with an incident light beam so as to form a back-scatter spot including a center, obtaining an image of said back-scatter spot, and analyzing the variations in brightness of said image at a plurality of points so as to determine said optical characteristic.

2. The method of claim 1 wherein said optical characteristic comprises the capacity of said substance to diffuse or absorb light.

3. The method of claim 1 wherein said substance comprises a cosmetic substance.

4. The method of claim 3 wherein said cosmetic substance comprises a dermatological substance.

5. The method of claim 3 including applying said cosmetic substance to a support.

6. The method of claim 1 including determining a reduced diffusion coefficient as a function of said variation in brightness of said plurality of points.

7. The method of claim 6 wherein at least two of said plurality of points are located at different distances from said center.

8. The method of claim 1 including determining the absorption coefficient as a function of said variation in brightness at said plurality of points.

9. The method of claim 8 wherein at least two of said plurality of points are located at different distances from said center.

10. The method of claim 5 wherein said support comprises keratinous fibers or cells.

11. The method of claim 5 wherein said support comprises an inert support.

12. The method of claim 5 wherein said support comprises a relief.

13. The method of claim 1 wherein said surface is substantially planar.

14. The method of claim 5 wherein said cosmetic substance is disposed on said support over an area of between about 0.5 and 5.0 cm$^2$.

15. The method of claim 14 wherein said cosmetic substance is disposed on said support over an area of between about 1 and 2 cm.

16. The method of claim 1 wherein said incident light beam comprises a beam of white light.

17. The method of claim 1 wherein said incident light beam comprises a beam of monochromatic light.

18. The method of claim 17 wherein said monochromatic light comprises red or blue light.

19. The method of claim 3 wherein said incident light beam has a substantially constant intensity over its entire cross-section.

20. The method of claim 19 wherein said incident light beam is produced by a light source, and including placing a spatial filter between said light source and said cosmetic substance.

21. The method of claim 1 wherein the angle of incidence of said incident light beam, relative to the normal of said surface, is between about 5° and 25°.

22. The method of claim 21 wherein the angle of incidence of said incident light beam, relative to the normal of said surface, is between about 10° and 20°.

23. The method of claim 1 including placing a mirror in the path of said incident light beam.

24. The method of claim 1 wherein said obtaining of said image comprises obtaining said image with a camera.

25. The method of claim 24 wherein said camera comprises a monochrome CCD camera.

26. The method of claim 1 including transmitting said image to a processing center for analysis.

27. The method of claim 26 including transmitting said image over the internet.

28. The method of claim 1 wherein said obtaining of said image comprises obtaining said image with an optical system having variable magnification.

29. The method of claim 1 wherein said incident light beam is produced by a light source, and including placing a polarizer in the path of said incident light beam between said light source and said surface.

30. The method of claim 29 wherein said obtaining of said image comprises obtaining said image through an analyzer.

31. The method of claim 1 wherein said obtaining of said image comprises obtaining said image in the absence of any interfering light.

32. The method of claim 1 including modulating said incident light beam, and wherein said obtaining of said image comprises obtaining said image synchronously.

33. The method of claim 5 including applying said cosmetic substance to said support at a thickness between about 7 µm and 20 µm.

34. The method of claim 33 wherein said thickness is substantially uniform.

35. The method of claim 5 wherein said cosmetic substance comprises a substance suitable for modifying at least one physico-chemical property of said support.

36. The method of claim 3 wherein said cosmetic substance is selected from the group consisting of foundation make-up, sunscreen, de-pigmenting cream, anti-wrinkle cream, and moisturizer.

37. A method for determining an optical characteristic of a substance comprising applying the substance on a zone of a support, illuminating the surface of the zone of the support with an incident light beam so as to form a back-scatter spot including a center, obtaining an image of said back-scatter spot, and analyzing the variations in brightness of said image at a plurality of points so as to determine said optical characteristic.

38. A method for determining at least one characteristic of a cosmetic substance comprising illuminating a first surface and a second surface with an incident light beam so as to form back-scatter spots, obtaining images of said back-scatter spots representing said first and second surfaces, analyzing the variation in brightness of said images at a plurality of points corresponding to said first and second surfaces, and determining said at least one characteristic as a function of said variations in brightness corresponding to said first and second surfaces, said first surface comprising skin or keratinous fibers and said second surface comprising said cosmetic substance applied to said skin or keratinous fibers.

39. The method of claim 38 wherein said at least one characteristic comprises an optical characteristic comprising the capacity of said cosmetic surface to diffuse or absorb light.

40. A method of determining variations in at least one optical characteristic of a cosmetic substance over time comprising applying said cosmetic substance to a support to provide a surface of said cosmetic substance, illuminating said surface of said cosmetic substance with an incident light beam so as to form a back-scatter spot, obtaining a first image of said back-scatter spot at a first instant, analyzing the variation in the brightness of said first image at a plurality of points so as to determine said at least one optical characteristic at a first instant, obtaining a second image of said back-scatter spot at a second instant, analyzing the variation in the brightness of said second image at a plurality of points so as to determine said at least one optical characteristic at a second instant, and determining said at least one optical characteristic over time as a function of said analyses of said variation in the brightness of said first and second images.

41. The method of claim 40 wherein said optical characteristics comprise the capacity of said cosmetic substance to diffuse or absorb light.

42. The method of claim 40 including effecting said surface after analyzing the variation in brightness of said first image and before obtaining said second image.

43. The method of claim 42 wherein said effecting of said surface comprises an action selected from the group consisting of washing said surface, exposing said surface to wind, and contacting said support with UV radiation.

44. The method of claim 40 wherein said at least one characteristic comprises the covering ability of said cosmetic substance.

45. The method of claim 40 wherein said cosmetic substance comprises a sunscreen, and wherein said at least one characteristic comprises the effectiveness of protection provided by said sunscreen as a function of time.

46. The method of claim 40 wherein said cosmetic substance comprises a de-pigmenting cream and wherein said at least one characteristic comprises the effectiveness of said de-pigmenting cream.

47. A method for prescribing a cosmetic substance to be applied to the skin comprising illuminating said skin with an incident light beam so as to form a back-scatter spot, obtaining an image of said back-scatter spot, analyzing the variation in brightness of said image at a plurality of points so as to determine at least one characteristic representing the capacity of said skin to diffuse or absorb light, and prescribing said cosmetic substance having a capacity to diffuse or absorb light corresponding to said determined at least one characteristic.

48. Apparatus for determining the capacity of a cosmetic substance to diffuse or absorb light comprising a light source for delivering a light beam capable of forming a light spot having a center on a predetermined surface, a camera for obtaining at least one image of said light spot, and an analyzer for analyzing the variation in brightness of said at least one image at a plurality of points of said light source so as to determine at least one data point representing said capacity of said cosmetic substance to diffuse or absorb light.

49. The apparatus of claim 48 wherein said camera comprises a monochrome CCD camera.

50. The apparatus of claim 48 wherein at least two of said plurality of points are located different distances from said center.

51. The apparatus of claim 48 wherein said light source comprises a laser.

52. The apparatus of claim 48 including a spatial filter, wherein said light beam passes through said spatial filter.

53. The apparatus of claim 48 including a mirror disposed in the path of said light beam.

54. The apparatus of claim 48 including a network connection for said analyzer and said camera.

55. The apparatus of claim 54 wherein said network comprises the internet.

56. A method for preparing a cosmetic substance for application to the skin comprising illuminating a predetermined area of said skin with an incident light beam so as to form a back-spatter spot, obtaining an image of said back-scatter spot, analyzing the variation in brightness of said image at a plurality of points so as to determine at least one data point representing the capacity of said skin to diffuse or absorb light, and preparing said cosmetic substance based upon said at least one data point.

57. The method of claim 56 wherein said cosmetic substance has the capacity to diffuse or absorb light corresponding to said capacity of said skin to diffuse or absorb light.

* * * * *

UNITED STATES PATENT AND TRADEMARK OFFICE
CERTIFICATE OF CORRECTION

PATENT NO. : 7,061,617 B2  
APPLICATION NO. : 10/458172  
DATED : June 13, 2006  
INVENTOR(S) : Bernard Querleux and Hervé Saint-Jalmes It is certified that error appears in the above-identified patent and that said Letters Patent is hereby corrected as shown below:

Column 11, line 10, "cm" should read --$Cm^2$--.

Signed and Sealed this

Fourteenth Day of November, 2006

JON W. DUDAS  
*Director of the United States Patent and Trademark Office*